United States Patent [19]

Miyata et al.

[11] Patent Number: 4,563,349

[45] Date of Patent: Jan. 7, 1986

[54] SUPEROXIDE DISMUTASE, ITS IMMOBILIZED FORM, AND THEIR PRODUCTION AND USE

[75] Inventors: Kouichi Miyata; Kazutaka Maejima; Katsumi Tomoda, all of Hyogo, Japan

[73] Assignee: Takeda Chemical Industries, Ltd., Osaka, Japan

[21] Appl. No.: 656,418

[22] Filed: Oct. 1, 1984

Related U.S. Application Data

[63] Continuation of Ser. No. 396,091, Jul. 7, 1982, abandoned, which is a continuation-in-part of Ser. No. 285,316, Jul. 22, 1981, abandoned.

[30] Foreign Application Priority Data

Jul. 30, 1980 [JP] Japan .................................. 55-105645
Jan. 14, 1982 [JP] Japan ..................................... 57-4750

[51] Int. Cl.$^4$ ........................ A61K 37/50; C12N 9/02; C12N 11/12; C12R 1/43
[52] U.S. Cl. ..................................... 424/94; 435/189; 435/179; 435/880; 435/881
[58] Field of Search ............... 435/179, 189, 880, 881; 424/94, 177

[56] References Cited

PUBLICATIONS

*The Journal of Biological Chemistry*, vol. 245, No. 22, pp. 6176-6181 (1970).
*Journal of Molecular Biology*, vol. 105, pp. 333-335 (1976).
*Superoxide and Superoxide Dismutase*, pp. 517-536 (1977) (see p. 518, lines 28-35) Academic Press.
*Current Microbiology*, vol. 1, No. 6, 1978, pp. 371-376.
*Journal of Bacteriology*, vol. 134, No. 1, Apr. 1978, pp. 229-236.
*Proceedings of the National Academy of Sciences of the U.S. of A.*, vol. 77, No. 2, pp. 1159-1163 (Feb. 1980).
*Advances in Inflammation Research*, vol. 1, pp. 273-280 (1979).
*Journal of General Applied Microbiology*, vol. 22, pp. 161-164.

*Primary Examiner*—Lionel M. Shapiro
*Attorney, Agent, or Firm*—Wenderoth, Lind & Ponack

[57] ABSTRACT

A novel superoxide dismutase is produced by cultivating a microorganism belonging to the genus Serratia. The superoxide dismutase is useful as an antiinflammatory agent.

An immobilized superoxide dismutase has properties of decreased antigenicity and increased antiinflammatory activity.

9 Claims, 7 Drawing Figures

Fig. 1

—○— Acetate buffer solution
—●— Phosphate buffer solution
—✧— Glycine sodium hydroxide buffer solution

SUPEROXIDE DISMUTASE, ITS IMMOBILIZED FORM, AND THEIR PRODUCTION AND USE

This application is a continuation of application Ser. No. 396,091, filed July 7, 1982 (abandoned concurrently with the filing of this application), which application is in turn a continuation-in-part application of application Ser. No. 285,316, filed July 22, 1981 (now abandoned).

This invention relates to superoxide dismutase, its immobilized form, and their production and use.

The present inventors undertook a diligent research for discovering a new superoxide dismutase and found that a microorganism belonging to the genus Serratia was able to produce such a new superoxide dismutase. And further study by the present inventors led to a finding that, when said enzyme is immobilized by binding it to a water-soluble carrier, excellent pharmacological effects such as decreased antigenicity and increased antiinflammatory activity are emerged. This finding was followed by a further series of studies which have resulted in the present invention described in detail hereinafter.

This invention is directed to (1) a superoxide dismutase produced by a microorganism belonging to the genus Serratia and its immobilized form, (2) a method of producing said superoxide dismutase by employing a superoxide dismutase-producing microorganism belonging to the genus Serratia and a method of producing an immobilized superoxide dismutase by binding superoxide dismutase to a water soluble carrier, and (3) an antiinflammatory agent which contains an effective amount of superoxide dismutase or its immobilized form.

In the present specification, the present superoxide dismutase produced by a microorganism belonging to the genus Serratia is sometimes referred to as "Serratia SOD" for short, and an immobilized enzyme comprising said superoxide dismutase and a carrier bond thereto is sometimes referred to as an "immobilized Serratia SOD" for short.

The present Serratia SOD is produced by cultivating a superoxide dismutase-producing microorganism belonging to the genus Serratia in a culture medium to thereby cause the microorganism to elaborate and accumulate the superoxide dismutase in the culture medium and harvesting the superoxide dismutase from the resulting culture broth.

The microorganism to be employed for the production of Serratia SOD is any of the microorganisms belonging to the genus Serratia and capable of producing Serratia SOD, inclusive of a mutant strain thereof. Among such microorganisms, there are mentioned *Serratia liquefaciens*, *Serratia marcescens*, *Serratia marinorubra*, and concretely mentioned *Serratia liquefaciens* IFO 12979, *Serratia marcescens* IFO 3046, *Serratia marcescens* IFO 3759 (ATCC 4002), *Serratia marcescens* IFO 3736 (ATCC 9986), *Serratia marcescens* ATCC 21074 and *Serratia marinorubra* IFO 12973 (ATCC 27614).

The above IFO 12979 strain was deposited with the Institute for Fermentation, Osaka, Japan on Apr. 29, 1969, the IFO 3046 strain in 1947, the IFO 3759 strain on Sept. 23, 1958, the IFO 3736 strain on June 21, 1958 and the IFO 12973 strain on Apr. 29, 1969. These strains are listed in the Institute for Fermentation, Osaka, List of Cultures, 1978, Sixth Edition.

The above ATCC 21074 strain was deposited with the American Type Culture Collection, U.S.A. on May 15, 1967, and the above ATCC 4002, ATCC 21074 and ATCC 27614 strains are listed in the American Type Culture Collection, Catalogue of Strains I, Fourteenth Edition, 1980 and Fifteenth Edition 1982. The above ATCC 9986 strain is listed in the American Type Culture Collection, Catalogue of Strains I, Fifteenth Edition, 1982.

The morphological characteristics of the *Serratia liquefaciens* IFO 12979 are described in Institute for Fermentation Research Communication, No. 7, p. 143-145, 1975, those of the *Serratia marcescens* IFO 3046 and IFO 3736 strains are the same as those described in Bergey's Manual of Determinative Bacteriology Eighth Edition, p. 326 (1974), those of *Serratia marcescens* IFO 3759 are described in Journal of Bacteriology vol. 11, p. 76-77 (1926), those of *Serratia marcescens* E-15 ATCC 21074 are described in U.S. Pat. No. 3,691,014 and Institute for Fermentation Research Communication No. 4, p. 1-11 (1969), and those of *Serratia marinorubra* IFO 12973 are described in Bulletin of Scripps Institute Oceanography vol. 5, p. 239 (1944).

Microorganisms of the genus Serratia, in general, are liable to undergo change in characteristics and can be easily mutated by means of artificial treatments such as irradiation with X-rays, ultraviolet rays or radiation, mutagenic agents (nitrosoguanidine, ethyleneimine, etc.). Any of the resulting mutants can be employed for the purposes of this invention unless they have lost the ability to produce the superoxide dismutase.

The production of the contemplated superoxide dismutase is carried out by cultivating said microorganism in a culture medium and harvesting and purifying the resulting elaboration product, which is the desired product, from said culture medium.

The culture medium may be liquied or solid, only if it contains nutrient sources which the particular strain of microorganism can utilize, although a liquid culture medium is desirable when mass production is contemplated.

Incorporated in such a medium are sources of nutrients which the microorganism can assimilate, digest or otherwise utilize, such as carbon sources, nitroben sources, inorganic materials, trace nutrients and so on. The carbon sources may for example be starch, dextrin, glucose, sucrose, etc., and the nitrogen sources may for example be corn steep liquor, soybean meal, extracted soybean meal, yeast extract, denucleated yeast, casein, cotton seed meal, nitrogen-containing compounds such as ammonium chloride, ammonium sulfate, etc. The inorganic materials include, for example, sodium salts (e.g. sodium chloride), phosphates (e.g. sodium phosphate), calcium salts (e.g. calcium carbonate), potassium salts (e.g. potassium chloride, potassium phosphate, magnesium salts (e.g. magnesium sulfate), manganese salts (e.g. manganese chloride, manganese carbonate), iron salts (e.g. iron chloride), zinc salts (e.g. zinc carbonate) and so on. The trace nutrients may for example be vitamins (e.g. vitamin $B_1$, $B_2$), fatty acid esters [e.g. esters (e.g. methyl or ethyl esters) of oleic acid, lauric acid, caproic acid, etc.)], nucleic acids (e.g. ribonucleic acid, deoxyribonucleic acid), related compounds of nuelcic acids (e.g. inosinic acid, guanylic acid, adenylic acid) and so on. For deforming purposes, oils, (e.g. soybean oil, corn oil, peanut oil), synthetic antifoams [e.g. Tween 20, 60 and 80 (Kao-Atlas Co. Ltd., Japan), Actocol (Takeda Chemical Industries, Ltd., Japan)], etc. may also be incorporated.

The cultivation method may for example be stationary culture, shake culture or aerated stir (submerged aerobic) culture. Submerged aerobic culture, in particular, is especially useful for production-scale runs. While cultural conditions vary with the condition and composition of medium, strain of microorganism, cultural method, etc., cultivation is desirably conducted at about 20° to 40° C. for about 10 to 100 hours, preferably, about 20 to 72 hours, the pH of the medium being about 4 to 9 and, preferably, about 6 to 8.

The desired enzyme is mostly accumulated intracellularly. This enzyme is harvested and purified by conventional purification procedures. It is advantageous to collect the cells from the culture broth by centrifugation, filtration or some other known separatory method, disrupt the cells by such a procedure as ultrasonication, grinding with glass beads, or a method involving the use of a surfactant or solvent, and extract the enzyme from the disrupted mass. In harvesting the enzyme, the same or other known separation and purification procedure in the field of art can be followed in any case to obtain a product of optional purity. Thus, the enzyme-containing disrupted mass is centrifuged or filtered to give a supernatant or filtrate. To this enzyme extract is added ammonium sulfate or acetone, and the resulting precipitate is collected by centrifugation, dissolved in a small quantity of water, desalted by dialysis and lyophilized, whereupon a crude enzyme powder is obtained. This crude enzyme powder can be purified by means employed conventionally for purification of enzymes. By way of illustration, gel filtration with Sephadex (Pharmacia Fine Chemicals AB, Sweden), column chromatography on diethylaminoethyl-cellulose (Serva Fine Biochimica, West Germany) or a like procedure can be followed to isolate superoxide dismutase. In this manner, superoxide dismutase can be separated and isolated in a desired purity.

The enzymological and chemical properties of the superoxide dismutase obtained in Example 2 which appears hereinafter are as follows.

(a) Activity: It dismutates a superoxide ion into a hydrogen peroxide molecule and an oxygen molecule.

(b) Substrate specificity: It acts on superoxide ion.

(c) Optimum pH range: The optimum pH range of this enzyme is about 7 to 8.

Figure 1:
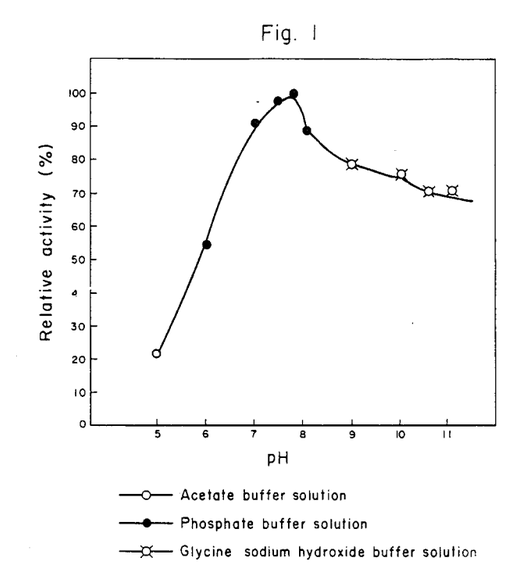

FIG. 1 shows a pH-activity curve of this enzyme.

(d) Stable pH range: The enzyme is stable in the pH range of about 6 to 11.

Figure 2:
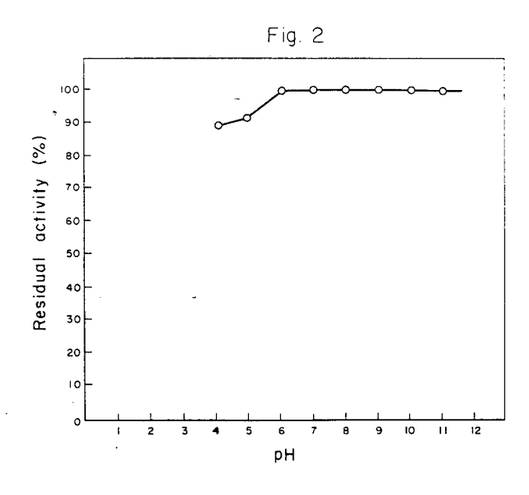

FIG. 2 shows a pH-stability curve of this enzyme.

(e) Optimum functional temperature: About 20° to 45° C.

(f) Thermostability (conditions of inactivation): The enzyme was treated at pH 7.8 and various temperatures for various time periods. The enzyme is stable at 37° C. for 60 minutes but is inactivated about 50% when treated at 50° to 60° C. for 60 minutes and almost 100% when treated at 80° C. for 5 minutes.

Figure 3:
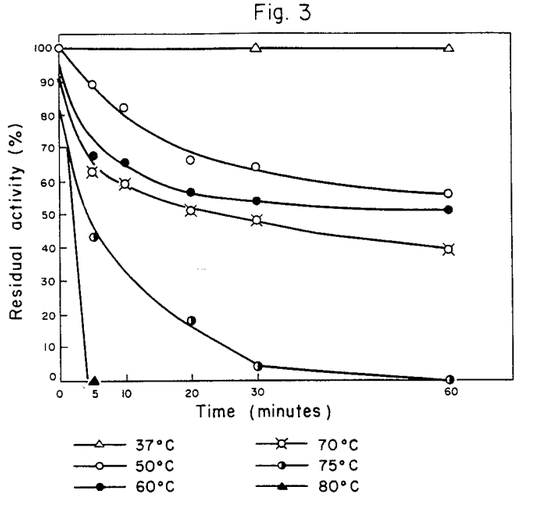

FIG. 3 shows a thermostability of this enzyme.

(g) Molecular weight: As determined by the gel filtration method using a Sephadex G-100 column [The Biochemical Journal 91, 222-233, 1964], this enzyme has a molecular weight of about $4.8 \times 10^4$. When the enzyme is first treated with 1% sodium laurylsulfate (SDS) and then subjected to polyacrylamide gel electrophoresis in the presence of the SDS [The Journal of Biological Chemistry 244, 5074-5080, 1969], the enzyme is found to have a molecular weight of about $2.4 \times 10^4$. These values indicate that this enzyme is a dimer consisting of subunits each having a molecular weight of about $2.4 \times 10^4$.

(h) Elemental analysis: C=48.90±2.0%; H=7.05±2.0%; N=14.80±2.0%

Figure 4:
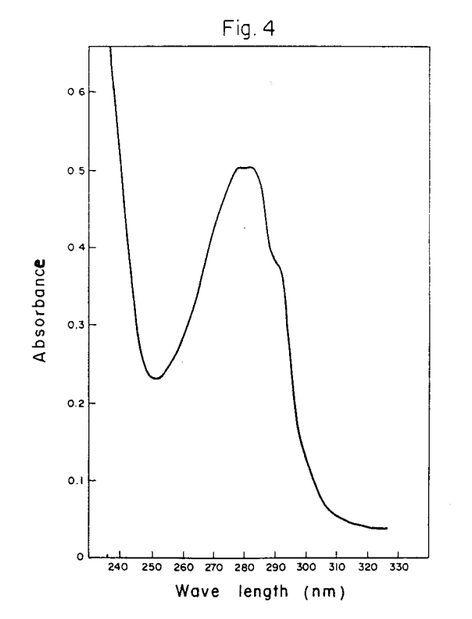
Figure 5:
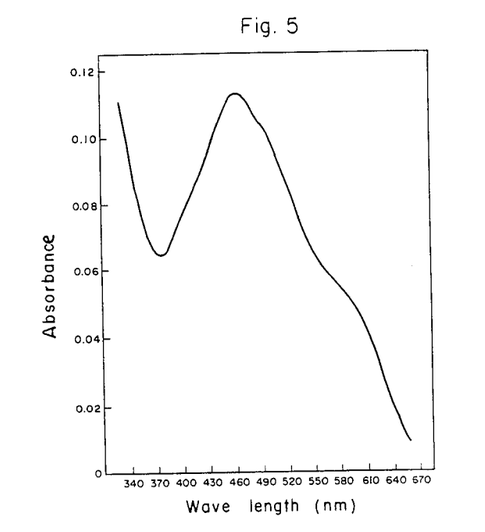

(i) Absorptions in the ultraviolet and visible regions of the spectrum: FIG. 4 shows an ultraviolet absorption spectrum of this enzyme and FIG. 5 shows a visible absorption spectrum of this enzyme.

In the UV region, this enzyme gives an absorption maximum at about 280 nm, an absorption minimum at about 253 nm and a shoulder at about 290 nm. The absorbance ratio (260 nm/280 nm) is 1.8. In the visible region, the enzyme shows an absorption maximum at about 470 to 475 nm, an absorption minimum at 375 to 380 nm and a shoulder at about 610 nm.

Figure 6:
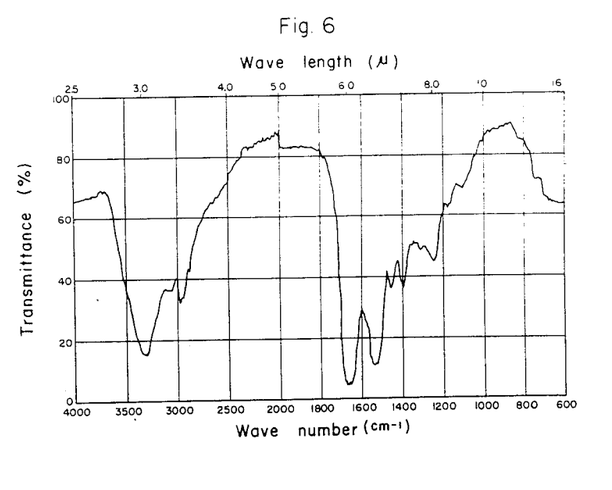

(j) Infrared absorption spectrum: FIG. 6 shows an infrared absorption spectrum of this enzyme measured by the KBr method. Characteristic absorptions are 3.02(s), 3.38(m), 6.00(s), 6.60(s), 6.95(m), 7.25(m), 8.10 (m), 8.50(w), 9.10(w).

(k) Molar extinction coefficient: The molar extinction coefficient of the enzyme at 280 nm is about $1.08 \times 10^5$ $M^{-1} \cdot cm^{-1}$.

(l) Amino acid analysis:

The enzyme is hydrolyzed with 6N-HCl at 110° C. for a predetermined time period (24–72 hrs.) and analyzed for amino acids by means of an amino acid analyzer. The values given in the following table denote the number of amino acid residues per molecule of the enzyme (mol. wt. = $4.8 \times 10^4$).

| Amino acid | Number of residues | Amino acid | Number of residues | Amino acid | Number of residues |
|---|---|---|---|---|---|
| Lysine | 28.8 | Tryptophan | 14.4 | Serine | 20.2 |
| Histidine | 13.9 | Aspartic acid | 47.0 | Glutamic acid | 40.3 |
| Arginine | 10.6 | Threonine | 18.7 | Proline | 13.9 |
| Glycine | 23.5 | Valine | 22.6 | Leucine | 28.3 |
| Alanine | 48.4 | Methionine | 5.3 | Tyrosine | 18.2 |
| Cysteine | 0 | Isoleucine | 10.6 | Phenylalanine | 19.3 |

(m) Analysis for metal: As determined by the atomic absorption method, this enzyme contains about 1.5 gram-atom of manganese. It is, therefore, clear that the enzyme is a Mn-superoxide dismutase.

(n) Isoelectric point is about pH 5.

The enzymatic potency assay procedure is as follows.

1. The method described in the Journal of Biological Chemistry 244, 6049-6055 (1969) is employed. Thus, a sample cell (length of light pass 1 cm) is filled with 1.5 ml of 100 mM phosphate buffer (pH 7.8), 0.5 ml of 60 μM cytochrome C, 0.5 ml of 0.6 mM ethylenediaminetetracetate sodium, 0.25 ml of 0.6 mM xanthine and 0.21 ml of the enzyme solution diluted with phosphate buffer (pH 7.8) to a measurable concentration, followed by addition of 0.04 ml of xanthine oxidase solution to make a total of 3.0 ml. The cell is set on a spectrophotometer and the reaction is initiated at 25° C. so as to measure the initial velocity (v) or reduction of cytochrome C at 550 nm. As a blank, the initial velocity (V) of reduction of cytochrome C in the presence of distilled water in lieu of the enzyme solution is also measured. With the amount of the enzyme causing a 50% inhibition of the initial velocity of reduction of cytochrome C under the above reaction conditions being taken as unity, the enzymatic potency is calculated by means of the following equation.

$$U/mg = \frac{(V) - (v)}{(v) \times \text{amount of enzyme (mg)}/1.0 \text{ ml reaction mixture}}$$

2. The active dye method described in Analytical Biochemistry 44, 276–287, 1971 can also be utilized. Thus, after polyacrylamide gel electrophoresis, the gel is immersed in 2.45 mM nitro blue tetrazolium for 20 minutes. Then, the gel is further immersed in a mixture of 28 mM tetraethylethylenediamine, 0.028 mM riboflavine and 36 mM potassium phosphate (pH 7.8) for 15 minutes. The gel is put in a test tube and exposed to the light rays of a 15-watt fluorescent lamp, whereupon the superoxide ion $O_2^-$ generated by photoreduction of riboflavine reduces the nitro blue tetrazolium so that the moiety other than that having superoxide dismutase activity forms a blue-formazan and is therefore dyed blue-purplish.

Proteins can be assayed by the method of Lowry [The Journal of Biological Chemistry 193, 265–275, 1951].

The superoxide dismutase according to this invention differs in physicochemical properties from the known superoxide dismutase. The known superoxide dismutase includes the one obtained from *Escherichia coli* B [The Journal of Biological Chemistry vol. 245, No. 22, pp. 6176–6181, 1970] and the one derived from *Bacillus stearothermophilus* [Journal of Molecular Biology, vol. 105, pp. 333–335, 1976]. The molecular weight of the superoxide dismutase derived from *Escherichia coli* is 39,500 and that of the superoxide dismutase from *Bacillus stearothermophilus* is 40,000. Since these weight figures are significantly different from the molecular weight of the enzyme of this invention which is about $4.8 \times 10^4$, the superoxide dismutase according to this invention is considered to be a novel enzyme.

The present immobilized Serratia SOD is produced by binding Serratia SOD to a water-soluble carrier.

The water-soluble carrier to be employed in the practice of the present invention includes, among others, water-soluble polysaccharides [e.g. dextrin, dextran, Ficoll Type 70 (polymer of sucrose, molecular weight about 70,000), Ficoll Type 400 (polymer of sucrose, molecular weight about 400,000) (Sigma Chemical Company, U.S.A.)], proteins or enzymes (e.g. serum albumin, hemoglobin, casein, α-amylase, β-amylase, trypsin, chymotrypsin) and water-soluble synthetic polymers (e.g. polyethylene glycol, polyvinyl alcohol).

Immobilization of Serratia SOD on a carrier may be effected by a binding method involving physical adsorption, ionic bonding or covalent bonding, for instance. More specifically, the immobilization may be carried out by the known methods described in Seikagaku Jikken Koza (Experiments in Biochemistry), vol. 5, pages 641–666, Tokyo Kagaku Dojin, 1975, Japan, or in Methods in Enzymology, vol. XLIV, pages 11–332, Academic Press, 1976, U.S.A. Thus, for example, cyanogen bromide is used for binding Serratia SOD to a water-soluble polysaccharide; glutaraldehyde or dicyclohexylcarbodiimide is used for binding to a protein or enzyme; and trichlorotriazine is used for binding to polyethylene glycol. Each reaction is desirably carried out, for example, in a neutral solution at or below room temperature (25° C.) so as to prevent inactivation of the dismutase. The resulting immobilized enzyme is separated from the remaining reagent by, for example, dialysis or gel filtration.

Serratia SOD has an antiinflammatory activity. Thus, for instance, when tested by the commonly known carrageenan-induced edema method [The Journal of Pharmacology and Experimental Therapeutics, 150, 328 (1965)], Serratia SOD (a sample having an activity of 3,000 U/mg) shows an overt inhibition of edema formation in the rat hind leg at an dose of 1.0 mg/kg or more under intravenous administration.

Effect on nystatin edema: A 1% (w/v) nystatin solution in physiological saline was injected subcutaneously into the paw of JCL-ICR mice at a dose of 0.025 ml. At the same time, Serratia SOD (about 11,000 to 12,000 U/mg protein) was administered to the same site by subcutaneous injection. This experiment was conducted according to the method described in Pharmacology, vol. 5, pp. 215–224 (1971). After six hours from the nystatin administration, the edema volume was measured. The results are set forth in the following table.

TABLE 1

| Treatment | Dose U/paw | No. of mice | Edema volume (mg) Mean ± S.E. | Inhibition (%) |
|---|---|---|---|---|
| Control | — | 10 | 120.45 ± 8.87 | — |
| Serratia SOD | 50 | 10 | 92.35 ± 4.38 | 23.3 |
| Serratia SOD | 500 | 10 | 83.71 ± 3.28 | 30.5 |

S.E. = standard error

As is clear from the above results, Serratia SOD inhibits nystatin edema.

The immobilized enzyme obtained by binding the Serratia SOD, which is obtained by the above method, to a water-soluble carrier bound thereto possesses, enzymatically, an increased thermal stability and, pharmacologically, a decreased antigenicity, an increased lipid-peroxide-formation-inhibiting activity and consequently an increased antiinflammatory activity, so that it can also be administered intravenously. Therefore, said immobilized enzyme has very useful properties for its administration to mammals, especially humans.

The following test results demonstrate the above properties.

Figure 7:
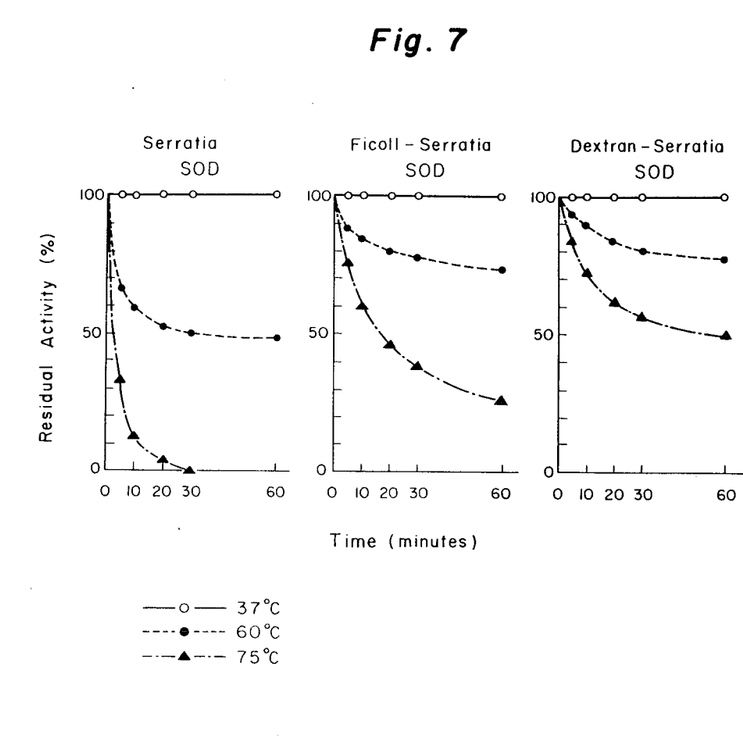

(1) Heat stability:

Serratia SOD and two kinds of immobilized Serratia SOD (Ficoll-Serratia SOD or dextran-Serratia SOD obtained in Examples 6 and 7, respectively) were stored in 0.1 M phosphate buffer (pH 7.8) at 37° C., 60° C. and 75° C. for certain periods and then assayed for the residual activity. FIG. 7 shows the results of thermal stability of the immobilized Serratia SOD. In FIG. 7, the activity of each enzyme at time 0 (zero) (1,000 U/mg) is expressed as 100%.

As is clear from said results, Ficoll-Serratia SOD and dextran-Serratia SOD each has an increased heat stability as compared with Serratia SOD.

(2) Antigenicity:

The antigenicity testing was performed by Ouchterlony's double diffusion test method as described in Rinsho Kensa Gijutsu Zensho (Techniques for Clinical Examinations), vol. 4 (edited by T. Kawai), page 85, Igaku Shoin, 1973, Japan or in Progr. Allergy, vol. 5, pages 1–78 (1958). Thus, a well, 3 mm in diameter, cut in a 1% agar plate (layer thickness 1 mm, 50 mM phosphate buffer, pH 7.0) was filled with 5 μl of an enzyme solution having the concentration given in Table 2 below, and another well with 5 μl of antiserum. After allowing the plate to stand at 4° C. for 5 days, the plate was examined for the presence of a line of immune precipitation. The antiserum used was obtained by injecting Serratia SOD (5 mg) subcutaneously into the back of a rabbit (female, 3 kg) repeatedly three times at 2-weeks intervals.

TABLE 2

| Enzyme | Immune response | |
|---|---|---|
| | Enzyme concentration (U/ml) | Immune precipitate |
| Serratia SOD | 150 | − |
| Serratia SOD | 300 | ± |
| Serratia SOD | 450 | + |
| Ficoll-Serratia SOD | 400 | − |
| Ficoll-Serratia SOD | 500 | ± |
| Ficoll-Serratia SOD | 600 | + |
| Dextran-Serratia SOD | 1000 | − |
| Dextran-Serratia SOD | 1500 | ± |
| Dextran-Serratia SOD | 2000 | + |

Notes: - absence, ± presence in a slight amount, + presence

As is clear from Table 2, the reactivity of Ficoll-Serratia SOD to the anti Serratia SOD serum is three fifths (3/5) of that of Serratia SOD, and the reactivity of dextran-Serratia SOD is as low as one fifth (1/5) of that of Serratia SOD.

(3) Inhibition of lipid peroxide formation:

To a solution of 10 mM sodium linolenate and 0.8% Tween 80 (Kao-Atlas Co. Ltd., Japan) in 50 mM phosphate buffer (pH 7.0), there was added each enzyme shown in Table 3 so as to be a concentration of 50 U/ml. The mixture was allowed to stand at 37° C. for 2 days and assayed for the lipid peroxide by the thiobarbiturate method described in Methods in Enzymology, vol. 52, p. 306, Academic Press, U.S.A., 1978, and the degree of inhibition of lipid peroxide formation was expressed as inhibition percentage based on the peroxide amount obtained in the control (no enzyme addition). The results are set forth in Table 3.

TABLE 3

| Enzyme | Inhibition on autoperoxidation of linoleic acid | |
|---|---|---|
| | Concentration (U/ml) | Inhibition (%) |
| — | 0 | 0 |
| Serratia SOD | 50 | 36 |
| Ficoll-Serratia SOD | 50 | 91 |
| Dextran-Serratia SOD | 50 | 78 |

As is clear from the above Table 3, Ficoll-Serratia SOD and dextran-Serratia SOD strongly inhibit the autoperoxidation of lipids as compared with Serratia SOD.

(4) Antiinflammatory activity:

According to the method described in Archives Internationales de Pharmacodynamie et de Therapie, vol. 144, p. 183 (1963), 0.5 ml of a 2% (w/v) carrageenan solution was injected subcutaneously into the back of a rat. Thirty minutes later, an enzyme set forth below in Table 4 was intravenously administered. After 24 hours from the administration of the enzyme, the abscess was excised and weighed for comparison with the control (physiological saline administration).

TABLE 4

| | Antiinflammatory activity against carrageenan-induced abscess | | | |
|---|---|---|---|---|
| Enzyme | Dose (U/rat kg) | No. of rats | Abscess wet weight (g) Mean ± standard error | Inhibition (%) |
| — | 0 | 7 | 2.017 ± 0.086 | — |
| Serratia SOD | 24,000 | 7 | 1.925 ± 0.085 | 4.6 |
| Ficoll-Serratia SOD | 24,000 | 7 | 1.738 ± 0.082 | 13.8* |
| Dextran-Serratia SOD | 24,000 | 7 | 1.483 ± 0.078 | 26.5** |

Significance test
*$P<0.05$
**$P<0.01$

As is clear from the above Table 4, Ficoll-Serratia SOD and dextran-Serratia SOD have stronger antiinflammatory activity against carrageenan-induced abscess in rats than Serratia SOD.

Serratia SOD is sparingly toxic and no death is encountered even when it is intraperitoneally administered to rats at a dose of 60 mg/kg. Even when 625 mg/kg of Serratia SOD was intraperitoneally administered to mice, no death was encountered. Furthermore, when Serratia SOD was intravenously administered to mice at a dose of 2,000 mg/kg, no death was observed. As for the immobilized Serratia SOD enzymes, they presumably have the same degree of toxicity as that of Serratia SOD, since no toxicity is observed for the carriers in the immobilized enzymes.

Serratia SOD and immobilized serratia SOD each has an antiinflammatory activity as mentioned above and accordingly is of use as an antiinflammatory agent.

The antiinflammatory agent contains an effective amount of Serratia SOD or immobilized Serratia SOD as an active ingredient in association with a pharmaceutically acceptable carrier or excipient therefor.

For the treatment of various acute or subacute inflammatory diseases or edema (e.g. arthritis, bronchitis, edema due to a bruise, burn) in mammalian animals (e.g. mouse, rat, rabbit, cat, dog, monkey, man), Serratia SOD or immobilized Serratia SOD can be administered orally or parenterally as formulated in a conventional manner into tablets, capsules, injections, ointments or other dosage forms at a daily dose of about 1 to 5 mg (as enzyme preparation) per kg.

Examples of the carrier for use in preparing the above pharmaceutical preparations are albumin, globulin, dextran, Ficoll Type 70 (polymer of sucrose, molecular weight about 70,000), Ficoll Type 400 (polymer of sucrose, molecular weight about 400,000) (Sigma Chemical Company, U.S.A.), lactose, dextran and starch. The production of pharmaceutical preparations may be carried out by employing a per se known method.

The following Examples are given to illustrate this invention in further detail without limiting its scope. Unless otherwise specified, percents (%) are weight-/volume percents (w/v %).

EXAMPLE 1

A 200 ml-conical flask was filled with 40 ml of a liquid medium containing 1.0% of solvent-extracted soybean meal, 1.5% of casein, 0.6% of diammonium phosphate, 0.1% of sodium chloride, 0.05% of potassium chloride, 0.02% of calcium chloride, 0.02% of magnesium sulfate, 1.0% of calcium carbonate, 0.0021% of zinc carbonate, 0.6% of soybean oil and 0.1% of Actocol (adjusted to pH 7.0), and was sterilized with steam at 120° C. for 20 minutes. The flask was inoculated with a loopful of one of the undermentioned strain of the genus Serratia and incubated at 28° C. on a rotary shaker revolving at 230 r.p.m. for 48 hours. The fermentation broth was centrifuged to separate the cells which were lyophilized at −20° C. A 10-gram portion of the cellular lyophilizate was taken and reconstituted at 30° C. Following addition of 40 ml of 20 mM phosphate buffer (pH 7.8), the cells were disrupted by ultrasonication (2A, 5 minutes). The disrupted cells were centrifuged to give a supernatant fluid. This supernatant was measured for superoxide dismutase activity by the above-described xanthine-xanthine oxidase-cytochrome C method and polyacrylamide gel electrophoresis method. The results are set forth below in the table. It is clear that in all strains of Serratia, Serratia SOD was intracellularly accumulated.

| Strain | Deposite No. | Activity (U/mg · protein) |
| --- | --- | --- |
| Serratia liquefaciens | IFO 12979 | 74 |
| Serratia marcescens | IFO 3046 | 67 |
| Serratia marcescens | IFO 3759 | 115 |
| Serratia marcescens | IFO 3736 | 91 |
| Serratia marinorubra | IFO 12973 | 200 |

EXAMPLE 2

(a) Harvesting the Cells

A 2-liter Sakaguchi flask was filled with 500 ml of a liquid medium of the same composition as described in Example 1 and, after sterilization, inoculated with *Serratia marcescens* IFO 3736. The flask was incubated at 28° C. on a rotary shaker revolving at 230 r.p.m. for 24 hours to give a seed culture. A 200-liter tank was charged with 100 l of a medium of the same composition as above and under sparging at the rate of 100 l/min., submerged aerobic culture was conducted at 28° C. The resulting fermentation broth was centrifuged to separate the cells which were lyophilized at −20° C.

(b) Preparing a Crude Enzyme Product

A 1.5-kg portion of the wetted cell was reconstituted at 30° C. and after addition of 3 l of 20 mM phosphate buffer (pH 7.8), the cells were disrupted in a Dynomill (Willy A. Bachofen Manufacturing Engineers, Switzerland) apparatus and centrifuged in a Sharples type centrifuge to give a clear supernatant. From this supernatant, the precipitate obtained with 30–70% (W/V) of ammonium sulfate was collected by centrifugation. This sediment was dissolved in 20 mM phosphate buffer containing a small amount of 0.1 M KCl (pH 7.0) and, in a cellulose tube, dialyzed against the same type of buffer for 3 days. The internal fluid, i.e. 150 ml of dialysate, was concentrated to 30 ml by ultrafiltration through a Diaflow UM-5 membrane [an ultrafiltration membrane of Amicon Far East Limited, U.S.A.]. The concentrate was loaded onto a column (4.0×66.0 cm) of Sephadex G-150 previously equilibrated with the same buffer solution and eluted with the same buffer to collect 210 ml of an enzymatically active fraction. To this fraction was added ammonium sulfate to a concentration of 70% (W/V) and the resultant precipitate was collected by centrifugation and dissolved in a small amount of water. In a cellulose tube, this solution was dialyzed against water for 3 days and the internal fluid was lyophilized to give 620 mg of a crude enzyme product. The specific activity of this product was 3600 U/mg·protein.

(c) Preparing a Pure Enzyme Product (i) Column Chromatography on Diethylaminoethyl-cellulose In a small amount of 20 mM tris-hydrochloric acid buffer (pH 9.0) was dissolved 620 mg of the crude enzyme obtained in (b), and in a cellulose tube, the solution was dialyzed against the same buffer for 3 days. The internal fluid, i.e. 80 ml of dialysate, was put on a column (2.5×45.0 cm) of diethylaminoethyl-cellulose previously equilibrated with the same buffer and the enzyme was eluted by increasing the concentration of sodium chloride in the same buffer linearly from 0 to 250 mM to collect 45 ml of an enzymatically active eluate.

(ii) Gel Filtration on Sephadex G-100

The enzyme solution obtained in (i) (45 ml) was put in a cellulose tube and dialyzed against 20 mM phosphate buffer containing 0.1 M of KCl. The internal fluid (60 ml) was concentrated to 6.0 ml by ultrafiltration through a Dyaflow UM-5 membrane. This concentrate was put on a column (2.6×74.0 cm) of Sephadex G-100 equilibrated with the same buffer as above and the enzyme was eluted with the same buffer to collect an enzymatically active eluate which was red-purple in color. The fractions thus obtained are constant in specific activity, and polyacrylamide gel electrophoresis shows that it was a single component product. The specific activity of this purified Serratia SOD (24 mg) was 12,000 U/mg·protein.

EXAMPLE 3

*Serratia marcescens* IFO 3759 was treated in the manner as Example 2 to give 1.5 kg of lyophilized cells and, then, 410 mg of crude enzyme therefrom. The specific activity of this enzyme product was 3630 U/mg·protein. This enzyme was further purified by the procedure as Example 2 to give a purified Serratia SOD. The specific activity of this pure product was 12,000 U/mg·protein.

EXAMPLE 4

*Serratia marinorubra* IFO 12973 was treated in the manner as Example 2 to give 1.5 kg of lyophilized cells and, thence, 830 mg of crude Serratia SOD. The specific activity of this enzyme was 3,800 U/mg·protein.

EXAMPLE 5

(a) Harvesting the Cells

A 2000 ml of Sakaguchi flask was filled with 500 ml of a liquid medium containing 1.0% of solvent-extracted soybean meal, 1.5% of casein, 0.6% of diammonium phosphate, 0.1% of sodium chloride, 0.05% of potassium chloride, 0.02% of calcium chloride, 0.02% of magnesium sulfate, 1.0% of calcium carbonate, 0.0021% of zinc carbonate, 0.6% of soybean oil and 0.1% of Actocol (adjusted to pH 7.0), and, after sterilization, inoculated with *Serratia marcescens* ATCC 21074. The flask was incubated at 28° C. on a rotary shaker revolving at 230 r.p.m. for 24 hours to give a seed culture. A 200-liter tank was charged with 100 l of a medium of the same composition as above and under sparging at the rate of 100 l/min., submerged aerobic culture was conducted at 28° C. The resulting fermentation broth was centrifuged to separate the cells which were lyophilized at −20° C.

(b) Preparing a Crude Enzyme Product

A 5-kg portion of the wetted cell was reconstituted at 30° C. and after addition of 10 l of 20 mM phosphate buffer (pH 7.8), the cells were disrupted in a Dynomill apparatus and centrifuged in a Sharples type centrifuge to give a clear supernatant. From this supernatant, the precipitate obtained with 30–70% (W/V) of ammonium sulfate was collected by centrifugation. This sediment was dissolved in 20 mM phosphate buffer containing a small amount of 0.1 M KCl (pH 7.0) and, in a cellulose tube, dialyzed against the same type of buffer for 3 days. The internal fluid, i.e. 530 ml of dialysate, was concentrated to 40 ml by ultrafiltration through a Diaflow-UM-5 membrane. The concentrate was loaded onto a column (4.0×66.0 cm) of Sephadex G-150 previously equilibrated with the same buffer solution and eluted with the same buffer to collect 550 ml of an enzymatically active fraction. To this fraction was added ammonium sulfate to a concentration of 70% (W/V) and the resultant precipitate was collected by centrifugation and dissolved in a small amount of water. In a cellulose tube, this solution was dialyzed against water for 3 days and the internal fluid was lyophilized to give 2070 mg of a crude enzyme product. The specific activity of this product was 3600 U/mg·protein.

(c) Preparing a Pure Enzyme Product

(i) Column Chromatography on Diethylaminoethyl-cellulose

In a small amount of 20 mM tris-HCl buffer (pH 9.0) was dissolved 2070 mg of the crude enzyme obtained in (b), and in a cellulose tube, the solution was dialyzed against the same buffer for 3 days. The internal fluid, i.e. 134 ml of dialysate, was put on a column (3.8×55.0 cm) of diethylaminoethyl-cellulose previously equilibrated with the same buffer and the enzyme was eluted by increasing the concentration of sodium chloride in the same buffer linearly from 0 to 250 mM to collect 54 ml of an enzymatically active eluate.

(ii) Gel Filtration on Sephadex G-100

The enzyme solution obtained in (i) (54 ml) was put in a cellulose tube and dialyzed against 20 mM phosphate buffer containing 0.1 M of KCl. The internal fluid (73 ml) was concentrated to 2.0 ml by ultrafiltration through a Dyaflow UM-5 membrane. This concentrate was put on a column (2.6×74.0 cm) of Sephadex G-100 equilibrated with the same buffer as above and the enzyme was eluted with the same buffer to collect an enzymatically active eluate which was red-purple in color. The fractions thus obtained were constant in specific activity, and polyacrylamide gel electrophoresis shows that it was a single component product. The specific activity of this Serratia SOD (2.07 mg) was 12,000 U/mg·protein.

EXAMPLE 6

To 1.5 g of Ficoll (Sigma Chemical Company, U.S.A.; molecular weight 70,000) activated with cyanogen bromide by the method described in Acta Chemica Scandinavica, volume 25, page 1855 (1971), there was added 0.3 g of Serratia SOD prepared in Example 5, and the reaction was carried out at 23° C. for a day. The reaction mixture was placed in a cellulose tube and dialyzed against distilled water for 3 days. Lyophilization of the internal fluid gave 1.7 g of Ficoll-Serratia SOD (1,000 U/mg).

This Ficoll-Serratia SOD is soluble in water, and even the concentration of 50 mg/ml (in physiological saline) can be attained without difficulty.

EXAMPLE 7

1.5 g of dextran (Wako Pure Chemical Industries, Japan; molecular weight 60,000 to 90,000) and 0.3 g of Serratia SOD obtained in Example 5 were treated in the manner described in Example 6 to give 1.7 g of dextran-Serratia SOD (1,000 U/mg).

This dextran-Serratia SOD is soluble in water, and even the concentration of 50 mg/ml (in physiological saline) can be attained without difficulty.

EXAMPLE 8

Enteric capsules are prepared by a conventional method employing the following ingredients:

| Serratia SOD prepared in Example 5 (3,600 U/mg) | 10 mg |
|---|---|
| Lactose | 46 mg |
| Corn Starch | 16 mg |
| Crystalline cellulose | 12 mg |
| Cellulose glycollic acid | 5 mg |
| Sorbitol | 10 mg |
| | 99 mg |
| | (per capsule) |

The daily dose of the above capsules for human adults is generally 2 capsules after each meal (3 times a day).

EXAMPLE 9

Enteric tablets are produced by a conventional method employing the following ingredients:

| Serratia SOD obtained in Example 5 (3,600 U/mg) | 10 mg |
|---|---|
| Lactose | 79 mg |
| Corn starch | 45.5 mg |
| Magnesium stearate | 0.5 mg |
| | 135 mg |
| | (per tablet) |

The daily dose of the above tablets for human adults is generally 2 tablets after each meal (3 times a day).

EXAMPLE 10

Enteric capsules are produced by a conventional method employing the following ingredients:

| Ficoll-Serratia SOD prepared in Example 6 (1,000 U/mg) | 40 mg |
|---|---|
| Lactose | 46 mg |
| Corn Starch | 16 mg |
| Crystalline cellulose | 12 mg |
| Cellulose glycollic acid | 5 mg |
| Sorbitol | 10 mg |
| | 129 mg |
| | (per capsule) |

The daily dose of the above capsules for human adulsts is generally 2 capsules after each meal (3 times a day).

EXAMPLE 11

Enteric tablets are produced by a conventional method employing the following ingredients:

| | |
|---|---|
| Dextran-Serratia SOD obtained in Example 7 (1,000 U/mg) | 40 mg |
| Lactose | 79 mg |
| Corn starch | 45.5 mg |
| Magnesium stearate | 0.5 mg |
| | 165 mg (per tablet) |

The daily dose of the above tablets for human adults is generally 2 tablets after each meal (3 times a day).

What we claim is:

1. Superoxide dismutase having the following properties:
   (a) Activity: to dismutate a superoxide ion into a hydrogen peroxide molecule and an oxygen molecule;
   (b) Substrate specificity: to act on superoxide ion;
   (c) Optimum pH range: about 7 to 8;
   (e) Stable pH range: about 6 to 11;
   (e) Optimum functional temperature range: about 20° to 45° C.;
   (f) Thermostability: stable at 37° C. for 60 minutes; Inactivated about 50% at 50°-60° C. in 60 minutes; Inactivated about 100% at 80° C. in 5 minutes;
   (g) Molecular weight: about $4.8 \times 10^4$ (by gel filtration method);
   (h) Elemental analysis: C. 48.90±2.0%, H. 7.05±2.0%, N. 14.80±2.0%,
   (i) Absorptions in the visible region of the spectrum; 470–475 nm (max.), 375–380 nm (min.), about 610 nm (shoulder);
   (j) Molar extinction coefficient: about $1.08 \times 10^5$ $M^{-1}.cm^{-1}$ at 280 nm;
   (k) Amino acid analysis:

| Amino acid | Number of residues |
|---|---|
| Glycine | 23.5 |
| Leucine | 28.3 | wherein the values denote the number of amino acid residues per molecule of the enzyme.

2. An antiinflammatory agent which contains an effective amount of superoxide dismutase having the following properties:
   (a) Activity: to dismutate a superoxide ion into a hydrogen peroxide molecule and an oxygen molecule;
   (b) Substrate specificity: to act on superoxide ion;
   (c) Optimum pH range: about 7 to 8;
   (d) Stable pH range: about 6 to 11;
   (e) Optimum functional temperature range: about 20° to 45° C.;
   (f) Thermostability: Stable at 37° C. for 60 mintues; Inactivated about 50% at 50°-60° C. in 60 minutes; Inactivated about 100% at 80° C. in 5 minutes;
   (g) Molecular weight: about $4.8 \times 10^4$ (by gel filtration method);
   (h) Elemental analysis: C. 48.90±2.0%, H. 7.05±2.0%, N. 14.8±2.0%,
   (i) Absorptions in the visible region of the spectrum: 470–475 nm (max.), 375–380 nm (min.), about 610 nm (shoulder);
   (j) Molar extinction coefficient: approx. $1.08 \times 10^5$ $M^{-1}.cm^{-1}$ at 280 nm;
   (k) Amino acid analysis:

| Amino acid | Number of residues |
|---|---|
| Glycine | 23.5 |
| Leucine | 28.3 | wherein the values denote the number of amino acid residues per molecule of the enzyme, as an active ingredient in association with a pharmaceutically acceptable carrier or excipient therefor.

3. An immoblized superoxide dismutase which is produced by reacting superoxide dismutase having the following properties:
   (a) Activity: to dismutate a superoxide ion into a hydrogen perioxide molecule and an oxygen molecule;
   (b) Substrate specificity: to act on superioxide ion;
   (c) Optimum pH range: about 7 to 8;
   (d) Stable pH range: about 6 to 11;
   (e) Optimum functional temperature range: about 20° to 45° C.;
   (f) Thermostability: stable at 37° C. for 60 minutes; Inactivated about 50% at 50°-60° C. in 60 minutes; Inactivated about 100° at 80° C. in 5 minutes;
   (g) Molecular weight: about $4.8 \times 10^4$ (by gel filtration method);
   (h) Elemental analysis: C. 48.90±2.08%, H. 7.05±2.08%, N. 14.80±2.08%,
   (i) Absorptions in the visible region of the spectrum: 470–475 nm (max.), 375–390 nm (min.), about 610 nm (shoulder);
   (j) Molar extinction coefficient: about $1.08 \times 10^5 M^{-1}.cm^{-1}$ at 280 nm;
   (k) Amino acid analysis:

| Amino acid | Number of residues |
|---|---|
| Glycine | 23.5 |
| Leucine | 28.3 | the values denote the number of amino acid residues per molecule of the enzyme, with a water-soluble carrier.

4. An immobilized superoxide dismutase according to claim 3, wherein the water-soluble carrier is water-soluble polysaccharide.

5. An immobilized superoxide dismutase according to claim 4, wherein the water-soluble carrier is dextran or Ficoll.

6. An antiinflammatory agent which contains an effective amount of an immbolized superoxide dismutase which is produced by reacting superoxide dismutase having the following properties:
   (a) Activity: to dismutate a superoxide ion into a hydrogen peroxide molecule and an oxygen molecule;
   (b) Substrate specificity: to act on superoxide ion;
   (c) Optimum pH range: about 7 to 8;
   (d) Stable pH range: about 6 to 11;
   (e) Optimum functional temperature range: about 20° to 45° C.;
   (f) Thermostability: Stable at 37° C. for 60 minutes; Inactivated about 50% at 50°-60° C. in 60 minutes; Inactivated about 100% at 80° C. in 5 minutes;

(g) Molecular weight about $4.8 \times 10^4$ (by gel filtration method);

(h) Elemental analysis: C. $48.90 \pm 2.0\%$, H. $7.05 \pm 2.0\%$, N. $14.80 \pm 2.0\%$, (i) Absorptions in the visible region of the spectrum: 470–475 nm (max.), 375–380 nm (min.), about 610 nm (shoulder);

(j) Molar extinction coefficient: approx. $1.08 \times 10^5$ $M^{-1} \cdot cm^{-1}$ at 280 nm;

(k) Amino acid analysis:

| Amino acid | Number of residues |
|---|---|
| Glycine | 23.5 |
| Leucine | 28.3 | wherein the values denote the number of amino acid residues per molecule of the enzyme,
with a water-soluble carrier, as an active ingredient in association with a pharmaceutically acceptable carrier or excipient therefor.

7. An antiinflammatory agent according to claim 6, wherein the water-soluble carrier is a water-soluble polysaccharide.

8. An antiinflammatory agent according to claim 7, wherein the water-soluble carrier is dextran or Ficoll.

9. A method of producing superoxide dismutase characterized by cultivating *Serratia marcescens* ATCC 21074 in a culture medium to thereby cause the microorganism to elaborate and accumulate superoxide dismutase in said medium and harvesting said superoxide dismutase from the resulting culture broth.

* * * * *